United States Patent [19]

Elliott

[11] Patent Number: 4,931,082
[45] Date of Patent: Jun. 5, 1990

[54] TRIAZOLE DERIVATIVES USEFUL AS PLANT GROWTH REGULATING AGENTS

[75] Inventor: Raymond Elliott, Near Reading, England

[73] Assignee: Imperial Chemical Industries PLC, London, England

[21] Appl. No.: 936,719

[22] Filed: Nov. 25, 1986

[30] Foreign Application Priority Data

Dec. 10, 1985 [GB] United Kingdom ............... 8530429

[51] Int. Cl.$^5$ ................. A01N 43/653; C07D 249/08
[52] U.S. Cl. ........................................... 71/92; 71/76; 548/101; 548/267.8; 548/268.6
[58] Field of Search ............ 548/262, 101; 71/92, 71/76

[56] References Cited

U.S. PATENT DOCUMENTS 4,414,210 11/1983 Miller et al. .................... 514/383
4,505,922 3/1985 Dager et al. .................... 574/383
4,507,140 3/1985 Sugavanam .................... 548/262
4,622,333 11/1986 Luntzseh et al. ................ 514/383

FOREIGN PATENT DOCUMENTS 0097425 1/1984 European Pat. Off. ............ 548/262
0096786 3/1984 European Pat. Off. ............ 548/262
0097426 4/1984 European Pat. Off. ............ 548/262
3242222 5/1984 Fed. Rep. of Germany ...... 548/262

OTHER PUBLICATIONS

Arnoldi et al., *Pestic. Sci.*, 13: 670–678 (1982).

Primary Examiner—Glennon H. Hollrah
Assistant Examiner—Patricia L. Morris
Attorney, Agent, or Firm—Cushman, Darby & Cushman

[57] ABSTRACT

This invention relates to heterocyclic compounds useful as plant growth regulating agents, to processes for preparing them, to compositions containing them and to methods of regulating plant growth using them.

7 Claims, No Drawings

TRIAZOLE DERIVATIVES USEFUL AS PLANT GROWTH REGULATING AGENTS

SUMMARY OF THE INVENTION

In European Patent Publication No. 0097425 there are described certain triazole and imidazole compounds having fungicidal activity.

According to the present invention there is provided a triazole having the general formula (I):

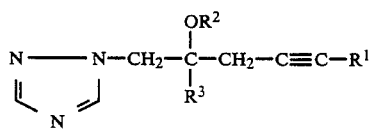

and stereoisomers thereof, wherein $R^1$ is an alkyl or haloalkyl group containing from 2 to 6 carbon atoms or a group $-(CH_2)n-R^4$ where n is from 0 to 2 and $R^4$ is cyclopropyl, cyclobutyl, cyclopentyl or cyclohexyl, optionally substituted by a lower alkyl group; $R^2$ is hydrogen, an alkyl group containing from 1 to 4 carbon atoms, an alkenyl group containing from 2 to 4 carbon atoms, an alkynyl group containing from 2 to 4 carbon atoms or a benzyl group; and $R^3$ is a tertiary butyl group optionally substituted by one or more halogen atoms; and salts, esters and metal complexes of the compounds of formula (1) wherein $R^2$ is hydrogen.

The compounds of the invention may contain chiral centres. Such compounds are generally obtained in the form of racemic mixtures. However, these and other mixtures can be seperated into the individual isomers by methods known in the art, and this invention embraces such isomers.

Preferred groups $R^2$ are hydrogen or methyl. $R^1$ is preferably a branched or straight chain alkyl group containing from 3 to 5 carbon atoms, and especially from to 4 carbon atoms or a haloalkyl group containing from 2 to 4 carbon atoms. When $R^1$ is a haloalkyl, it preferably contains a single halogen atom. Preferred halogen atoms are chlorine, bromine and fluorine, and especially chlorine. When $R^1$ is the group $-(CH_2)n-R^4$, n is preferably $R^3$ may be the tertiary butyl group, that is the group:

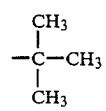

The tertiary butyl group may be optionally substituted by one or more halogen atoms, for example one or more fluorine atoms to give groups such as:

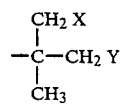

wherein X is Cl or F and Y is Cl, F or H. $R^3$ is preferably unsubstituted t-butyl or t-butyl substituted by a single halogen atom. Preferred halogen atoms are fluorine, chlorine and bromine, and especially fluorine and chlorine.

The present invention includes salts, esters and metal complexes of the compounds of formula (I) wherein $R^2$ is hydrogen. As examples of esters there may be mentioned for example acetates or benzoates. As examples of salts there may be mentioned toluene sulphonate salts, dodecyl benzene sulphonate salts, hydrochloride salts, hydrobromide salts, ortho- phosphate salts and nitrate salts. Without limitation of the generality of the above statement, the present invention also includes any compound which breaks down in agrochemical use to form a compound of formula (I).

Examples of the compounds of the invention are shown in Table I below in which the different values for $R^1$ and $R^2$ in the general formula (I) above are presented and $R^3$ has the structure:

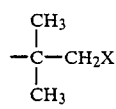

where X is as indicated in Table I.

TABLE I

| Compound No | $R^1$ | $R^2$ | X | M.p.t (°C.) |
|---|---|---|---|---|
| 1 | $-CH(CH_3)CH_2CH_3$ | H | H | 42–44 |
| 2 | $-CH_2CH_2CH_2CH_3$ | H | H | oil |
| 3 | $-CH_2CH_2CH_3$ | H | H | 54–56 |
| 4 | $-CH_2CH(CH_3)CH_3$ | H | H | 45–50 |
| 5 | $-CH(CH_3)CH_3$ | H | H | 45–48 |
| 6 | $-C(CH_3)_3$ | H | H | 55–58 |
| 7 | $-CH_2CH(CH_3)CH_2CH_3$ | H | H | oil |
| 8 | $(-CH_2CH_2CH(CH_3)CH_3$ | H | H | gum |
| 9 | $(-CH(CH_3)CH_2CH_2CH_3)$ | H | H | 44 |
| 10 |  | H | H | 38.5–41 |
| 11 | $-CH_2CH_3$ | H | H | 60–63.5 |
| 12 | $-CH_2CH_2CH_2Cl$ | H | H | oil |
| 13 | $-CH_2CH_2CH_3$ | H | F | 50–51 |
| 14 | $-CH_2CH(CH_3)_2$ | H | F | 49–50.5 |
| 15 | $-CH_2CH_2CH_3$ | H | Cl | 61–62 |
| 16 | $-CH_2CH_2CH_3$ | $CH_3$ | H | oil |
| 17 | $-CH_2CH_2CH_3$ | $CH_2CH_3$ | H | oil |

TABLE I-continued

| Compound No | R¹ | R² | X | M.p.t (°C.) |
|---|---|---|---|---|
| 18 | cyclopentyl | H | H | oil |
| 19 | —CH₂CH(CH₃)₂ | CH₃ | H | oil |
| 20 | —CH₂CH(CH₃)₂ | —CH₂CH=CH₂ | H | oil |
| 21 | —CH₂CH(CH₃)₂ | —CH₂C≡CH | H | oil |
| 22 | —CH₂CH(CH₃)₂ | —CH₂—C₆H₅ | H | oil |
| 23 | —CH₂CH₂Cl | H | H | gum |
| 24 | —CH₂CH(Cl)CH₃ | H | H | gum (1:1 mixture of diastereoisomers |
| 25 | —CH(Cl)CH₂CH₂CH₃ | H | H | gum mixture of diastereoisomers |
| 26 | —CH₂CH(Cl)CH₂CH₃ | H | H | oil (mixture of diastereoisomers) |
| 27 | —CH₂CH₂CH(Cl)CH₃ | H | H | oil |
| 28 | —CH₂CH(CH₃)₂ | —C(=O)—C₆H₅ | H | oil |

Examples of salts of Compound No 3 of Table I are shown in Table II below in which the acid from which the salt is derived is shown in column 1. Examples of salts of compound No. 4 of Table I are shown in Table III below.

TABLE II

| Acid | Melting Point of salt with Compound No. 3 (°C.) |
|---|---|
| HNO₃ | 88–93 |
| H₃PO₄ | Low melting solid |

TABLE III

| Acid | Melting Point of salt with Compound No. 4 (°C.) |
|---|---|
| H₂SO₄ | off-white solid |
| 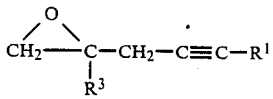 | 127.5–131 |
| HNO₃ | 96–99 |
| H₃PO₄ | 59.5–64.5 |
| HCl | 124–135 |

Compounds of general formula (I) wherein R² is H may be prepared by reacting a compound of general formula (II):

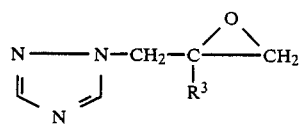  (II)

with an organometallic compound which may be represented by the general formula (III):

$$R^1\text{—}C\equiv C\text{—}M \quad (III)$$

wherein R¹ is as defined above and M is a metal which is preferably lithium, magnesium or aluminium. The reaction conveniently takes place in a solvent such as diethyl ether or tetrahydrofuran at −80° C. to +80° C. preferably in an inert atmosphere. The product maybe worked up by quenching with a proton donor. When M is magnesium the organometallic compound is more specificly $R^1\text{—}C\equiv C\text{—}Mg$ halogen.

The compound of general formula (I) wherein R² is H may also be prepared by reacting a compound of general formula (IV) or (V):

$$\text{Hal—CH}_2\text{—}\underset{R^3}{\underset{|}{\overset{OH}{\overset{|}{C}}}}\text{—CH}_2\text{—C}\equiv\text{C—R}^1 \quad (IV)$$

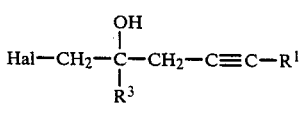  (V)

in which R¹ is as defined above and Hal is a halogen atom (preferably chlorine or bromine atom) with 1,2,4- triazole either in the presence of an acid binding agent (for example potassium carbonate) or in the form of one of its alkali metal salts in a convenient solvent.

Suitably the compound of general formula (IV) or (V) is reacted at 20°–120° C. with the sodium salt of 1,2,4-triazole (the salt can typically be prepared by adding either sodium hydride or sodium methoxide to 1,2,4-triazole in a convenient solvent such as acetonitrile, methanol, ethanol or dimethylformamide). The product can be isolated by pouring the reaction mixture into water and extracting the product with a suitable organic solvent e.g. diethyl ether, ethyl acetate or dichloromethane.

The compounds of general formula (I) wherein $R^2$ is H may also be prepared by reacting a compound of general formula (VI):

with an organometallic compound which may be represented by the general formula (VII):

$$R^1-C\equiv C-CH_2M$$

wherein $R^1$ is as defined above and M is a metal which is preferably magnesium or aluminium. The reaction conveniently takes place in a solvent such as diethyl ether or tetrahydrofuran at −80° C. to +80° C. preferably in an inert atmosphere. The product may be worked up by quenching with a proton donor. When M is magnesium the organometallic is more specifically $R^1C\equiv CCH_2Mg$ halogen. Usually the product is obtained as one component in a mixture and requires separation from this mixture for example using chromatography.

A compound of general formula (I) wherein $R^1$ is halo alkyl may be prepared as described above, for example by the addition of an organometallic reagent such as (VII) wherein $R^1$ is haloalkyl to a compound of general formula (VI). Alternatively the starting material wherein $R^1$ is haloalkyl may be replaced by a starting material wherein $R^1$ is replaced by $R^1$ where $R^1$ is hydroxyalkyl, or a derivative of hydroxyalkyl in which the hydroxyl group is protected for example as an ether, such as tert-butyldimethylsilyl ether or tetrahydropyranyl ether or as an ester, for example the paratoluene sulphonate.

The hydroxyl group or its derivative may then be transformed by one or more steps as set out in the literature into the required haloalkyl compound.

The ethers (wherein $R^2$ is alkyl) and the esters of the invention are made from the hydroxy compounds by reacting them with the appropriate halide, acid chloride or acid anhydride in the presence of a suitable base.

Compounds (IV) and (V) can be prepared by methods similar to those used in the literature e.g. Zh.Obshch. Kim., 1976, 46(4)855; CA 85(3)21533w. Compounds of formula (VII) wherein $R^3$ is halo-tertiarybutyl may be prepared by methods set out in the literature, for example DE 2820361 and DE 3025242.

The plant growth regulating effects of the compounds are manifested as, for example, by a stunting or dwarfing effect on the vegetative growth of woody and herbaceous mono- and di-cotyledonous plants. Such stunting or dwarfing may be useful, for example, in peanuts, cereals (such as wheat, barley and rice), oil seed rape, field beans, sunflowers, potatoes and soya bean where reduction in stem height, with or without further advantageous effects such as stem strengthening, thickening and shortening, internode shortening, increased buttress root formation and more erect stem and leaf orientation, may reduce the risk of lodging and may also permit increased amounts of fertilizer to be applied. The stunting of woody species is useful in controlling of the growth of trees under power lines etc.

The growth of trees acting as windbreaks, for example in orchards, may be controlled to prevent the need for excessive cutting back of foliage. Control of the growth of conifers may be useful in plantation management. Compounds which induce stunting or dwarfing may also be useful in modifying the stem growth of sugar cane thereby increasing the concentration of sugar in the cane at harvest; in sugar cane, the flowering and ripening may be controllable by applying the compounds. Stunting of peanuts can assist in harvesting. Growth retardation of grasses can help maintenance of grass swards. Examples of suitable grasses are Strenotaphrumsecundatum (St. Augustine grass), Cynosuruscristatus, Loliummultiflorum and *perenne*, Agrostistenuis, Cynodondactylon (Bermuda grass), Dactylisglomerata, Festuca spp. (e.g. *Festuca rubra*) and Poa spp. (e.g. Poa pratense). The compounds may stunt grasses without significant phytotoxic effects and without deleteriously affecting the appearance (particularly the colour) of the grass; this makes such compounds attractive for use on ornamental lawns and on grass verges. They may also have an effect on flower head emergence in, for example, grasses. The compounds can also stunt weed species present in the grasses; examples of such weed species are sedges (e.g. Cyperus spp.) and dicotyledonous weeds (e.g. daisy, plantain, knotweed, speedwell, thistle, docks and ragwort). The growth of non-crop vegetation (e.g. weeds or cover vegetation) can be retarded thus assisting in the maintenance of plantation and field crops. In fruit orchards, particularly orchards subject to soil erosion, the presence of grassover is important. However excessive grass growth requires substantial maintenance. The compounds of the invention could be useful in this situation as they could restrict growth without killing the plants which would lead to soil erosion; at the same time the degree of competition for nutrients and water by the grass would be reduced and this could result in an increased yield of fruit. In some cases, one grass species may be stunted more than another grass species; this selectivity could be useful, for example, for improving the quality of a sward by preferential suppression of the growth of undesirable species.

The dwarfing may also be useful in miniaturising ornamental, household, garden and nursery plants (e.g. poinsettias, roses, chrysanthemums, carnations, tulips and daffodils).

As indicated above, the compounds can also be used to stunt woody species. This property can be used to control hedgerows or to shape or reduce the need for pruning, of fruit trees (e.g. apples, pears, cherries, peaches, vines etc). Some coniferous trees are not significantly stunted by the compounds so the compounds could be useful in controlling undesirable vegetation in conifer nurseries.

The plant growth regulating effect may (as implied above) manifest itself in an increase in crop yield; or in an ability in orchards and other crops to increase fruit set, pod set and grain set.

In the potato, vine control in the field and inhibition of sprouting in the store may be possible.

Other plant growth regulating effects caused by the compounds include alteration of leaf angle and changes in leaf morphology (both of which may permit increased light interception and utilization) and promotion of tillering in monocotyledonous plants. Improved light interception is of value in all major world crops, e.g. wheat, barley, rice, maize, soya, sugarbeet, potatoes, plantation crops and orchard crops. The leaf angle effect may be useful for example in altering the leaf orientation of, for example, potato crops thereby letting more light into the crops and inducing an increase in photosynthesis and tuber weight. By increasing tillering in monocotyledonous crops (e.g. rice), the number of flowering shoots per unit area may be increased thereby increasing the overall grain yield of such crops. In addition better control and modification of hierarchical relationships is possible both in vegetative and reproductive stages of monocotyledonous and dicotyledenous plant growth, especially in cereals such as wheat, barley, rice and maize, whereby the number of flowering shoots per unit area may be increased and the size distribution of grains within the ear may be modified in such a way as to increase yield. In the treatment of rice plants, or rice crops the invention compounds can be applied, e.g. as granules or a granular formulation, for example as slow release granules, to nursery boxes, paddy water and other like cultivation loci and media. Paddy rice may be treated by submerged application of granules. In grass swards, especially amenity grass, an increase in tillering could lead to a denser sward which may result in increased resilience in wear; and to increased yields and better quality of forage grass, e.g. improved digestibility and palatability.

The treatment of plants with the compounds can lead to the leaves developing a darker green colour. In dicotyledonous plants such as soyabean and cotton, there may be promotion of sideshooting.

The compounds may inhibit, or at least delay, the flowering of sugar beet (and thereby may increase sugar yield) or otherwise modify the flowering patterns in many other crops. They may also reduce the size of sugar beet without reducing significantly the sugar yield thereby enabling an increase in planting density to be made. Similarly in other root crops (e.g. turnip, swede, mangold, parsnip, beetroot, yam and cassava) it may be possible to increase the planting density.

The compounds could be useful in restricting the vegetative growth of cotton thereby leading to an increase in cotton yield. Crop yields may also be increased by improvement of the harvest index (i.e. the harvested yield as a proportion of the total dry matter produced) by altering dry matter partitioning. This applies to all the aforementioned root, pod, cereal, tree, plantation and orchard crops.

The compounds may be useful in rendering plants resistant to stress since the compounds can delay the emergence of plants grown from seed, shorten stem height and delay flowering; these properties could be useful in preventing frost damage in countries where there is significant snow cover in the winter since then the treated plants would remain below snow cover during the cold weather. Further the compounds may cause drought or cold resistance in certain plants.

When applied as seed treatments at low rates the compounds may have a growth stimulating effect on plants.

It is to be understood that not all the compounds of the present invention will necessarily show all the above mentioned plant growth regulating effects. There may be advantages in compounds which have a broad spectrum of plant growth regulating effects against a wide range of species. However, equally useful are compounds which have a high specific activity with respect to a particular species and/or plant growth regulating effect.

The Examples show that the compounds of the present invention are generally very effective as growth retardants on a wide range of species, especially on small grain cereals such as wheat, barley and rice, on large grain cereals such as maize, and dicotyledonous species such as apples. The compounds generally show excellent reduction of interligular length, which is one indication of internode length reduction in mature plants and consequent limitation of the susceptibility of cereals to lodging. On woody species such as apples the compounds act as general retardants providing scope for their use as field management aids. The compounds generally have a substantial green up effect associated with the activity and in cereals can influence tillering which may be lead to increased ear number at maturity and hence increases in yield. Certain of the compounds of the present invention are substantially more active as growth retardants on rice and barley than on apples, and on rice and barley are active even at the lower rates of application. The compounds are generally however active at the higher rate on apples and more importantly for this species, good symptomology is associated with the activity.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.01 to 15, preferably 0.1 to 5, kg per hectare is used. With the use of biodegradable polymeric slow release granules rates of 1 to 10 g per hectare are feasible; whilst electrodynamic spraying techniques may also deploy lower rates of application. However, on certain plants even application rates within these ranges may give undesired phytotoxic effects. Routine tests may be necessary to determine the best rate of application of a specific compound for any specific purpose for which it is suitable.

The compounds may be used as such for plant growth regulating purposes but are more conveniently formulated into compositions for such usage. The invention thus provides a plant growth regulating composition comprising a compound of general formula (I) as hereinbefore defined, or a salt, ester or metal complex thereof; and, optionally, a carrier or diluent.

The invention also provides a method of regulating plant growth, which comprises applying to the plant, to seed of a plant or to the locus of a plant or seed, a compound, or a salt, ester or metal complex thereof, as hereinbefore defined, or a composition containing the same.

The compounds, salts' metal complexes, and esters can be applied in a number of ways, for example they can be applied, formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour; or as slow release granules. Application can be to any part of the plant, bush or tree, for example to the foliage, stems, branches or roots, or to soil surrounding the roots, or to the seed before it is planted; or to the soil generally, to paddy water or to hydroponic culture systems. The invention compounds may also be injected into plants or trees and they may also be sprayed onto vegetation using electrodynamic spraying techniques.

The term "plant" as used herein includes seedlings, bushes and trees.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions of the present invention may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a micro-encapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising the compound of general formula (I) or a salt, ester or metal complex thereof.

The compositions may also be in the form of liquid preparations for use as dips or sprays which are generally aqueous dispersions or emulsions containing the active ingredient in the presence of one or more surfactants e.g. wetting agent(s), dispersing agent(s), emulsifying agent(s) or suspending agent(s); or which are spray formulations of the kind suitable for use in electrodynamic spraying techniques. The foregoing agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), and the concentrate is to be diluted with water before use. These concentrates often should be able to withstand storage for prolonged periods and after such storage be capable of dilution with water in order to form aqueous preparations which remain homogeneous for a sufficient time to enable them to be applied by conventional and electrodynamic spray equipment. The concentrates may conveniently contain up to 95%, suitably 10–85%, for example 25–60%, by weight of the active ingredient(s) These suitably contain organic acids (e.g. alkaryl or aryl sulphonic acids such as xylenesulphonic acid or dodecyl benzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% to 10%, or 0.01% to 10%, by weight of active ingredient(s) may be used.

The compositions of this invention can comprise also one or more additional compound(s) having biological activity, e.g. compounds having similar or complementary fungicidal or plant growth activity or compounds having plant growth regulating, herbicidal or insecticidal activity.

The additional fungicidal compound can be, for example, one which is capable of combating ear diseases of cereals (e.g. wheat) such as Septoria, Gibberella and Helminthosporium spp., seed and soil borne diseases and downy and powdery mildews on grapes and powdery mildew and scab on apple etc. Examples of suitable additional fungicidal compound are imazalil, benomyl, carbendazim, thiophanate-methyl, captafol, captan, sulphur, triforine, dodemorph, tridemorph, pyrazophos, furalaxyl, ethirimol, tecnazene, dimethirimol, bupirimate, chlorothalonil, vinclozolin, procymidone, iprodione, metalaxyl, forsetyl-aluminium, carboxin, oxycarboxin, fenarimol, nuarimol, fenfuram, methfuroxan, nitrotal-isopropyl, triadimefon, thiabendazole, etridiazole, triadimenol, biloxazol, dithianon, binapacryl, quinomethionate, guazatine, dodine fentin acetate, fentin hydroxide, dinocap, folpet, dichlofluanid, ditalimphos, kitazin, cycloheximide, dichlobutrazol, a dithiocarbamate, prochlorez, a copper compound, a mercury compound, 1-(2-cyano-2-methoxyiminoacetyl)-3-ethyl urea, fenaponil, ofurace, propiconazole, etaconazole and fenpropemorph and fenpropidine.

The compounds of general formula (I) can be mixed with soil, peat or other rooting media for the protection of plants against seed-borne, soil-borne or foliar fungal diseases.

Suitable additional insecticides are Pirimor, Croneton, dimethoate, Metasystox, pyrethroid insecticides and formothion.

The other, additional, plant growth regulating compound can be one which controls weeds or seedhead formation, improves the level or longevity of the plant growth regulating activity of the compounds of general formula (I), selectively controls the growth of the less desirable plants (e.g. grasses) or causes the compound of general formula (I) to act faster or slower as a plant growth regulating agent. Some of these other agents will also be herbicides.

Examples of suitable plant growth regulating compounds, which can display synergy in admixture, or use, with the invention compounds are the gibberellins (e.g. GA$_3$, GA$_4$ and GA$_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acids (e.g. triiodobenzoic acid), morphactins (e.g. chlorfluorecol), maleic hydrazide, glyphosate, glyphosine, long chain fatty alcohols and acids, dikegulac, fluoridamid, mefluidide, substituted quaternary ammonium and phosphonium compounds (e.g. chlormequat* chlorphonium, phosphonl D or mepiquat*), ethephon, carbetamide, methyl-3,6-dichloroanisate, daminozide*, asulam, abscisic acid, isopyrimol, 1-(4-chlorophenyl)-4,6-dimethyl-2-oxo-1,2-dihydropyridine-3-carboxylic acid, hydroxybenzonitriles (e.g. bromoxynil), difenzoquat*, benzoylprop-ethyl 3,6-dichloropicolinic acid, uniconazole, triapenthanol, flurpirimidol, paclobutrazol, tetcyclacis tecnazene and amidichlor. Synergy will be most likely to occur with those of the foregoing which are quaternary ammonium compounds and with those marked with an asterisk.

For certain applications, for example in the injection to the compounds of the invention into trees or plants, it is desirable that the compounds have a relatively high solubility in water, for example a solubility in excess of 30 parts per million. The compounds may be used as an aqueous solution or may be formulated for injection, for example as a solution in a lower alcohol.

For certain applications it is also desirable that the compound has a low persistancy in soil to prevent carry-over to adjacent crops or even crops planted subsequently in the same soil. Preferably the compound for use in such applications has a half life in the soil of less than 20 weeks.

The invention is illustrated by the following Examples in which infra red analysis is expressed in terms of $\nu$ max (CM$^{-1}$), NMR data is expressed in terms of $S_H$ and mass spectroscopy analysis is expressed in terms of m/e.

EXAMPLE I

Preparation of 2,2-dimethyl-3-hydroxy-3-(4-methyl-hex-2-yne-1-yl)-4-(1,2,4-triazol-1-yl)-butane (Compound No 1 of Table I.

Stage 1

Preparation of the epoxide of formula:

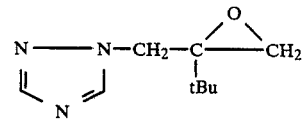

To a stirred mixture of 2,2-dimethyl-4-(1,2,4-triazol-1-yl)-butan-3-one (30 g), trimethylsulphoxonium iodide (47 g), and tetra-n-butyl ammonium bromide (0.3 g), in toluene (125 ml) was added a 50% aqueous solution of potassium hydroxide (45 ml). The resulting mixture was stirred at 70° C. for 3 hours. The mixture was then partitioned between ethyl acetate and water. The aqueous fraction was further extracted three times with ethyl acetate, and the combined organic extracts were washed twice with water and brine, dried over magnesium sulphate and concentrated in vacuo to give a yellow oil (27 6 g). The crude product was chromatographed on silica gel, eluting with 1:1 ether/petrol, and then 100% ether to give the title compound as a yellow oil (25.3 g) which crystallised to give a yellow solid.

NMR (100 mHz, CDCl$_3$)δ: 1.04 (9H,s), 1.92 (1H,d), 2.74 (1H,d), 4.56 (2H,AB) 7.88 (1H,s), 8.08 (1H,s).

Stage 2

To a mixture of ethyl magnesium bromide (3.7 ml of a 3.0 molar solution in diethyl ether) and THF (10 ml) was added 3-methyl-1-pentyne (0.9 g). The mixture was heated under reflux for 30 minutes then cooled to room temperature. A solution of the epoxide described in Stage 1 of Example 1 (1.0 g) in THF (10 ml) was added and the mixture heated under reflux for 1 hour. The mixture was partitioned between ethyl acetate and water. The aqueous fraction was extracted with ethyl acetate and the combined organic extracts washed with water and brine, dried over magnesium sulphate and concentrated in vacuo. Column chromatography of the crude product on silica gel eluting with diethyl ether (50–70%) in petrol gave the title compound as a yellow solid (0.95 g)(42°–44° C. melting point).

Nmr (270 mHz, CDCl$_3$)δ: 0.94 (3H,t), 1.08 (12H,cmplx), 1.4 (2H,m), 2.1 (1H,d), 2.28 (1H,m), 2.34 (1H,d), 3.47 (1H,s), 4.30 (1H,d), 4.56 (1H,d), 7.96 (1H,s), 8.22 (1H,s).

IR (nujol): 3160–3650, 3130 cm$^{-1}$.

Analysis C$_{15}$H$_{25}$N$_3$O, requires: C,68.40; H,9.57; N,15.95% found: C,68.40; H,9.30; N,15.70% m/e 263, 262, 248, 206, 181, 168, 83, 57.

EXAMPLE 2

Preparation of 2,2-dimethyl-3-hydroxy-3-(hept-2-yne-1-yl)-4-(1,2,4-triazol-1-yl)-butane (Compound No 2 of Table I).

To a mixture of ethyl magnesium bromide (3.7 ml of a 3.0 molar solution in diethyl ether) and tetrahydrofuran (40 ml) under nitrogen at room temperature, was added 1-hexyne (0.9 g). The mixture was heated under reflux for 30 minutes then cooled to room temperature. To the reaction mixture was added a solution of the epoxide, described in Stage 1 of Example 1 (1.0 g) in tetrahydrofuran (10 ml) and the mixture was heated under reflux for 1 hour. The reaction mixture was partitioned between ethyl acetate and water. The aqueous fraction was extracted with ethyl acetate and the combined organic extracts were washed with water and brine, dried over magnesium sulphate and concentrated in vacuo. Column chromatography on silica eluting with diethyl ether (50–70%) in petrol gave the title compound as a yellow oil (1.0 g). Nmr (100 mHz, CDCl$_3$)δ: 0.7–1.04 (3H,cmplx), 1.08 (9H, s), 1.1–1.6 (4H,cmplx), 1.8–2.7 (4H,cmplx), 3.44 (1H,s), 4.26 (1H,d), 4.56 (1H,d), 7.98 (1H,s), 8.24 (1H,s).

Analysis C$_{15}$H$_{25}$N$_3$O requires: C,68.40; H,9.57; N,15.95%: found: C,68.38; H,9.83; N,15.69%.

IR (film) 3150–3600, 3120 cm$^{-1}$.

m/e 263, 262, 248, 230, 206, 168, 83, 57.

EXAMPLE 3

Preparation of 2,2-dimethyl-3-hydroxy-3-(hex-2-yne-1-yl)-4-(1,2,4-triazol-1-yl)-butane (Compound No 3 of Table I).

The procedure of Example 2 was followed using 1-pentyne (1.1 ml) in place of the 1-hexyne. Column chromatography of the crude product on silica gel eluting with diethyl ether (50–70%) in petrol gave the title compound as a yellow solid (0.95 g)(54°–56° C. melting point).

Nmr (100 mHz, CDCl$_3$)δ: 0.92 (3H,t), 1.08 (9H,s), 1.18–2.66 (2H,cmplx), 1.92–2.64 (4H,cmplx), 3.42 (1H,s), 4.30 (1H,d), 4.58 (1H,d), 7.98 (1H,s), 8.24 (1H,s).

Analysis: C$_{14}$H$_{23}$N$_3$O, requires: C,67.44; H,9.30; N,16.85%; found: C,67.62; H,9.34; N,16.57%.

IR (Nujol): 3150–3600, 3130 cm$^{-1}$.

m/e: 219, 234, 221, 192, 168, 83, 57.

EXAMPLE 4

Preparation of 2,2-dimethyl-3-hydroxy-3-(5-methyl-hex-2-yne-1-yl)-4-(1,2,4-triazole-1-yl)-butane (Compound No 4 of Table 1).

The procedure of Example 2 was followed using 4-methyl-1-pentyne (0.9 g) in place of the 1-hexyne. Column chromatography of the crude product on silica gel eluting with diethyl ether (50–70%) in petrol gave the title compound as a yellow solid (0.71 g)(45°–50° C. melting Nmr (100 mHz, CDCl$_3$)$_{67}$: 0.96 (6H,d), 1.08 (9H,s), 1.6–2.7 (5H,cmplx), 3.42 (1H,s), 4.30 (1H,d), 4.60 (1H,d), 7.98 (1H,s), 8.20 (1H,s).

Analysis C$_{15}$H$_{25}$N$_3$O, requires: C,68.40; H,9.57; N,15.95%; found: C,68.29; H,9.99; N,15.95%

IR (film): 3150–3650, 3130 cm$^{-1}$.

m/e: 262, 248, 206, 168, 83, 57.

EXAMPLE 5

Preparation of 2,2-dimethyl-3-hydroxy-3-(4-methylpent-2-yne-1-yl)-4-(1,2,4-triazol-1-yl)-butane (Compound No 5 of Table I).

To a mixture of ethyl magnesium bromide (5.5 ml of a 3.0 molar solution in diethyl ether) and tetrahydrofuran (50 ml) was added 3-methyl-1-butyne (1.13 g). The mixture was heated under reflux for 30 minutes then cooled to room temperature. A solution of the epoxide described in Stage 1 of Example 1 (1.5 g) in tetrahydrofuran (10 ml) was added and the mixture heated under relux for 1 hour. The mixture was partitioned between ethyl acetate and water. The aqueous fraction was extracted with ethyl acetate and the combined organic extracts washed with water and brine, dried over magnesium sulphate and concentrated in vacuo. Column chromatography of the crude product on silica gel eluting with diethyl ether (50–70%) in petrol gave the title compound as a yellow solid (1.2 g)(45°–48° C. melting point).

Nmr (100 mHz, CDCl$_3$)δ: 1.0–1.3 (15H,cmplx), 1.90–2.70 (3H,cmplx), 3.46 (1H,s), 4.26 (1H,d), 4.58 (1H,d), 7.98 (1H,s), 8.24 (1H,s).

Analysis: C$_{14}$H$_{23}$N$_3$O, requires: C,67.44; H,9.30; N,16.85%; found: C,67.44; H,9.65; N,16.66%.

IR (Nujol): 3050–3600 cm$^{-1}$.

m/e: 234, 192, 168, 83, 57.

EXAMPLE 6

Preparation of 2,2-dimethyl-3-hydroxy-3-(4,4-dimethylpent-2-yne-1-yl)-4-(1,2,4-triazol-1-yl)-butane (Compound No 6 of Table I).

To a solution of ethyl magnesium bromide (3.7 mls of a 3M solution in ether) in dry tetrahydrofuran (20 mls) under nitrogen at room temperature was added dropwise t-butyl acetylene (0.9 g). The resulting mixture was heated at reflux for 30 minutes then cooled to room temperature. A solution of the triazolyl epoxide prepared in Stage 1 of Example 1 (1.81 g) in dry tetrahydrofuran (10 mls) was then added dropwise. The resultant mixture was heated at reflux for 2 hours then cooled and quenched by the cautious addition of water (2 mls). The solvent was removed in vacuo and the residue partitioned between water and ether. The aqueous was further extracted twice with ether. The combined etheral extracts were washed with brine, dried over magnesium sulphate and concentrated in vacuo to give a pale yellow oil (2.15 g) chromatography on silica gel using gradient elution (ether (60–100%) in petrol) gave the title compound (0.83 g) as a pale yellow oil which solidified on standing (melting point 55°–58° C.).

Nmr (CDCl$_3$)δ: 1.08 (9H,s), 1.20 (9H,s), 2.04, 2.53 (2H,2d(ABq)J 16Hz, 3.47 (1H,s), 4.28 (2H,2d(ABq)J 14Hz), 7.95 (1H,s), 8.22 (1H,s).

IR (film): 3050–3650, 3130 cm$^{-1}$.

m/e: 263, 262, 248, 245, 230, 206, 181, 168.

EXAMPLE 7

Preparation of 2,2-dimethyl-3-hydroxy-3-(5-methyl-hept-2-yne-1-yl)-4-(1,2,4-triazol-1-yl)-butane (Compound No 7 of Table 1).

The procedure of Example 6 was followed using 4-methyl-hex-1-yne (1.13 g) in place of the t-butyl acetylene and gave an orange oil (2.5 g). Chromatography on silica gel using 80% ether in petrol as the eluant gave the title compound (1.61 g) as a pale yellow oil.

Nmr (CDCl$_3$)$_\delta$: 0.87 (3H,tJ8Hz), 0.94 (3H,dJ8Hz), 1.08 (9H,s), 1.1–1.6 (3H,cmplx), 2.03 (2H, cmplx), 2.15, 2.52 (2H,2dtJ16 Hz,2 Hz), 3.44 (1H,s), 4.30, 4.54 (2d(ABq)J 16 Hz), 7.95 (1M,s), 8.22 (1H,s).

IR (film): 3000–3600 cm$^{-1}$.

m/e: no M$^+$, 262, 244, 220, 168.

Analysis: C$_{16}$H$_{27}$N$_3$O requires: C,69.27; M,9.81; N,15.15%; found: C,69.05; M,9.87; N,14.88%.

EXAMPLE 8

Preparation of 3-(1,2,4-triazol-1-yl-methyl)-2,2,9-tri-trimethyl-dec-5-yn-3-ol (Compound No 8 of Table I)

To a solution of 5-methylhex-1-yne (2.65 g) in dry tetrahydrofuran (30 ml) under nitrogen was added a solution of ethyl magnesium bromide in diethyl ether (9.2 ml of 3M). The resulting mixture was then refluxed for 0.5 h. After cooling to room temperature, a solution of 1-t-butyl-1-(1,2,4-triazol-1-yl-methyl)-oxirane (2.5 g) in dry tetrahydrofuran (10 ml) was added and the reaction mixture refluxed for 2 h. After cooling the mixture was poured carefully into water and extracted with ether (2×200 ml). The ethereal layer was washed successively with water and brine solution, dried over anhydrous magnesium sulphate and the solvent removed. The resulting gum was then chromatographed (silica gel, Merck Act.7731, petrol/diethyl ether solution) to give the product as a clear gum (2.95 g, 77%), b.p. 200° C./0.6 mmHg Analysis: Found: C, 69.3; H,9.4; N, 15.3.

C$_{16}$H$_{27}$N$_3$O requires C, 69.3; H, 9.8; N, 15.2%;

IR film: 3600, 2925, 1360, 1270, 1200, 1130, 1080, 1020, and 680 cm$^{-1}$;

NMR: (90 MHz CDCl$_3$) 0.88 (6H, d, J 7 Hz), 1.08 (9H, s), 1.18–1.78 (3H, m), 1.94–2.18 (2H, m), 2.32 (2H, qt, J 18 and 1.8 Hz), 3.34 (1H, s), 4.38 (2H, q, J 12.6 Hz), 7.92 (1H, s), 8.19 (1H, s);

m/e: 278 (M$^+$+1), 262, 234, 220, and 168 (100%).

EXAMPLE 9

Preparation of 3-(1,2,4-triazol-1-yl-methyl)-2,2,7-trimethyl-dec-5-yn-3-ol (Compound No 9 of Table I)

To a solution of 3-methylhex-1-yne (2.65 g) in dry tetrahydrofuran (30 ml) under nitrogen was added a solution of ethyl magnesium bromide in diethyl ether (9.2 ml of 3M). The resulting mixture was then refluxed for 0.5 h. After cooling to room temperature, a solution of 1-t-butyl-1-(1,2,4-triazol-1-yl-methyl)oxirane (2.5 g) in dry tetrahydrofuran (10 ml) was added and the reaction mixture refluxed for 2 h. After cooling the mixture was poured carefully into water and extracted with ether (2×200 ml). The ethereal layer was washed successively with water and brine solution; dried over anhydrous magnesium sulphate and the solvent removed. The resulting gum was then chromatographed (silica gel, Merck Art.7731, petrol/diethyl ether elution) to give the product as a white solid (2.7 g, 71%), m.p. 44° C.

Analysis: Found: C, 68.9; H, 10.1; N, 15.2.

C$_{16}$H$_{27}$N$_3$O requires C, 69.3; H, 9.8; N, 15.2%;

IR (nujol): 3300,2900, 1440, 1370, 1090, and 680 cm$^{-1}$;

NMR 90 MHz; CDCl$_3$: 0.78–1.2 (6H, m), 1.1 (9H, s), 1.2–1.62 (4H, m), 1.94–2.72 (3H, m), 3.34 (1H, s), 4.42 (2H, d, J 12.6 Hz), 7.94 (1H, s), 8.21 (1H, s);

m/e: 278 (M$^+$+1), 262, 234, 220, and 168 (100%).

EXAMPLE 10

Preparation of 2,2-dimethyl-3-hydroxy-3-(4-cyclopropyl-but-2-yne-1-yl)-4-(1,2,4-triazol-1-yl)butane (Compound No. 10 of Table I).

Stage 1

Preparation of 2,2-dimethyl-3-hydroxy-3-propargyl-4-(1,2,4-triazol-1-yl)-butane

In dry apparatus under argon was placed magnesium turnings (1.44 g, 0.060 g.at) covered with dry diethyl ether (10 mls). Mercuric chloride (0.05 g) was added at 15° C. followed by a few mls of propargyl bromide (5.34 g, 0.045M) in dry diethyl ether (15 mls). When the mixture went cloudy, an ice/salt cooling bath was applied and the remaining propargyl bromide solution was gradually added dropwise with stirring at such a rate as to maintain reaction. The mixture was then stirred at 0° C. for 1 hour. A solution of triazolylpinacolone (5.0 g, 0.030M) in dry dichloromethane (20 mls) was gradually added dropwise to the stirred mixture keeping temperature below 10° C. The mixture was stirred at 20° C. overnight. To the resultant thick suspension was added aqueous ammonium chloride solution with cooling. The mixture was extracted with ethylacetate several times and the combined organic layers washed with water then brine. The product was dried over anhydrous magnesium sulphate and concentrated in vacuo to give a pale yellow oil. Chromatography on silica gel using diethylether as eluent gave an oil which gradually crystallised to an off-white solid (4.3 g; mpt. 65°–7° C.).

NMR (CDCl$_3$)$_\delta$: 1.10 (9H,s); 2.02 (1H,s); 2.34 (2H,cmplx); 3.87 (1H,s); 4.47 (2H,cmplx); 7.96 (1H,s); 8.24 (1H,s).

IR (nujol) cm$^{-1}$: 3550–3050, 3240, 3300, 3148, 2125.

m/e: No M$^+$, 206, 168, 158, 192.

Stage 2

To liquid ammonia (approx 50 ml) at −60° C. was added a small piece of lithium (from 0.25 g, 36 mmol) followed by a spatula tip full of ferric nitrate. The remaining lithium was added gradually and the reaction mixture stirred until the blue colour had been discharged and a grey suspension was left (approx 40 mins). To the reaction mixture was added a solution of the product of stage 1 (2.5 g, 12 mmol) in tetrahydrofuran (10 ml) and the mixture was stirred for 2 hours, allowing the bath temperature to rise to −25° C. The bath was then cooled to −40° C. and cyclopropyl methyl bromide (2.3 ml, 24 mmol) was added. The reaction mixture was allowed to warm to room temperature overnight. The reaction mixture was partitioned between ethyl acetate and 20% ammonium chloride solution, and the aqueous portion was further extracted with ethyl acetate. The combined organic extracts were washed with water and brine, dried over anhydrous magnesium sulphate and concentrated in vacuo to give a brown gum (3 g). Column chromatography of the crude product on silica gel eluting with diethyl ether (20–100%) in petrol gave the title compound, as a pale yellow oil (2 g) which on standing crystallised to give a pale yellow solid (mp. 38.5°–41° C.).

NMR (CDCl$_3$, 270 MHz)$_\delta$: 0.16 (2H,m); 0.48 (2H,m); 0.90 (1H,m); 1.08 (9H,s); 2.12 (3H,m); 2.54 (1H,m); 3.50 (1H,s); 4.32 (1H,d); 4.59 (1H,d); 7.96 (1H,s); 8.25 (1H,s).

m/e: No M$^+$, 260, 246, 168, 83, 70, 57.

IR (Film): 3150–3550, 3130, 3070 m$^{-1}$.

Analysis C$_{15}$H$_{23}$N$_3$O, Requires: C, 68.93; H, 8.87; N, 16.08%; Found C, 68.66; H, 8.89; N, 16.07%.

EXAMPLE 11

Preparation of 2,2-dimethyl-3-hydroxy-3-(6-chloro-hex-2-yne-lyl)-4-(1,2,4-triazol-lyl)-butane (Compound No. 12 of Table I).

To a stirred solution of 5-chloropent-1-yne (2.3g, 22 mmol) in dry tetrahydrofuran (20 ml), under nitrogen at room temperature, was added ethyl magnesium bromide (7.5 ml of a 3.0 molar solution in diethyl ether). After an initial exothermic reaction, the reaction mixture was heated under reflux for 15 minutes then cooled to room temperature. A solution of the epoxide prepared in Stage 1 of Example 1 (1.0 g, 11 mmol) in tetrahydrofuran (40 ml) was added and the mixture heated under reflux for 3 hours. The reaction mixture was partitioned between ethylacetate and water. The aqueous portion was further extracted with ethyl acetate, then the combined organic extracts were washed with water and brine, dried over magnesium sulphate and concentrated in vacuo. Chromatography of the crude product on silica gel eluting with ethyl acetate (50%) in hexane gave the title compound, as a pale yellow oil (1.0 g).

NMR (CDCl$_3$, 270 MHz)$_\delta$: 1.08 (9H,s); 1.84 (2H,m); 2.20 2.20 (1H,m); 2.25 (2H,m) (1H,m); 3.50 (1H,s); 3.58 (2H,t); 4.32 (1H,d); 4.52 (1H,d); 7.96 (1H,s); 8.20 (1H,s)

m/e: No M+, 226, 158, 150, 122, 83, 70, 57, 43.

IR (film): 3150–3650, 3120 cm$^{-1}$.

Analysis: C$_{14}$H$_{22}$N$_3$O,Cl Requires: C, 59.25; H, 7.8; N, 14-81%; Found: C, 59.34; H, 7.49; N, 14.21%.

EXAMPLE 12

Preparation of 1-fluoro-2,2-dimethyl-3-hydroxy-3-(hex-2-yne-lyl)-4-(1,2,4-triazol-1-yl) butane (Compound No. 13 of Table I).

To a stirred suspension of magnesium turnings (2.5 equivalents in dry ether—20 ml) was added a catalytic amount of mercuric chloride (about 25 mg). On cooling to 0° C, there was added 1-bromohex-2-yne (2 equivalents 3.22 g; 20 mmol), prepared by the general method disclosed in Bull. Soc. Fr. 1971, 4546. After 1 hour a solution of 3,3-dimethyl-4-fluoro-1-(1′, 2′,4′-triazol-1′-yl)-butan-2-one (1 equivalent; 1.85 g; 10 mmol) in dry tetrahydrofuran (35 ml) was slowly added and stirred for 16 hours. The reaction was poured into water and extracted with ether (2×250 ml). The organic layer was collected, dried over magnesium sulphate and the solvent removed. Flash chromatography (silica gel, petrol/ether elution) gave the product, melting point 50°–51° C.

Analysis: Found: 63.9; H, 9.0; N, 15.5; C$_{14}$H$_{22}$FN$_3$O requires C, 62.9; H, 8.3; N, 15.7%.

IR: 3275, 3125, 2925, 1450, 1375, 1200, 1000, 900, 775, 680, 650, 600 cm$^{-1}$;

NMR (90 MHz; CDCl$_3$) 0.99 (3H,t, J=6 Hz), 1.12 (6H,m), 1.52 (2H, dt, J=6 and 6 Hz), 2.0–2.7 (4H,m), 3.9 (1H,s), 4.5 (2H,d, J=47 Hz), 4.54 (2H,dd, J=12.6 and 28.8 Hz), 8.0 (1H,s), 8.24 (1H,s);

m/e: 268 (M+H+), 186 (100%).

EXAMPLE 13

1-Fluoro-2,2-dimethyl-3-hydroxy-3-(5-methyl-hex-2-ynelyl)-4-(1,2,4-triazol-1-yl)-butane (Compound No. 14 of Table I) was prepared by the general method of Example 12, using as starting materials:

1-bromo-5-methylhex-2-yne (7 g, 40mmol) and 3,3-dimethyl-4-fluoro-1-(1′, 2′, 4′-triazol-1′-yl)butan-2-one (3.7 g, 20 mmol). The title compound (370 mg, 6.6%) had a melting point of 49°–50° C.

Analysis. (Found: C, 65.4; H, 9.0; N, 14.8. C$_{15}$H$_{24}$FN$_3$O requires C, 64.0; H, 8.6; N, 14.9%);

IR: 3250, 2950, 1280, 1200, 1140, 1080, 1000, 910, 860, 775, 680, 650, 600 cm$^{-1}$;

NMR (90 MHz, CDCl$_3$): 0.96 (6H, d, J=7.2 Hz), 1.1 (6H, s), 1.74 (1H, m), 1.96–2.26 (3H, m), 2.4–2.74 (1H, m), 3.8 (1H, s), 4.46 (2H, d, J=46.8 Hz), 4.52 (2H, dd, J=12.6 and 27 Hz), 7.97 (1H, s), 8.22 (1H, s);

m/e: 282 (M+H+), 239, 238, 186 (100%).

EXAMPLE 14

1-Chloro-2,2-dimethyl-3-hydroxy-3-(hex-2-yne-lyl)-4-(1,2,4-triazol-1-yl)-butane (Compound No. 15 of Table I) was prepared by the general method of Example 12, using as starting material:

1-bromohex-2-yne (3.22g, 20mmol) and 4-chloro-3,3-dimethyl-1-(1′,2′,4′-triazol-1′-yl)butan-2-one (2.02 g, 10 mmol). The product (1 g) was purified by preparative HPLC (silica gel, CH$_2$Cl$_2$ elution) to give the title compound (400 mg, 14.2%), mp 61°–62° C.

Analysis: Found: C, 60.5; H, 9.1; N, 15.0. C$_{14}$H$_{22}$ClN$_3$O requires C, 59.3; H, 7.8; N, 14.8%

IR: 3150, 2900, 1500, 1450, 1375, 1270, 1200, 1120, 1080, 1000, 960, 805, 720, 680, 600 cm$^{-1}$;

NMR (90 MHz; CDCl$_3$): 0.97 (3H, t, J=7 Hz), 1.19 (6H, s), 1.5 (2H, dt, J=7 and 7 Hz), 1.9–2.22 (3H, m), 2.44–2.74 (1H, m), 3.66 (1H, s), 3.78 (2H, s), 4.55 (2H, dd, J=12.6 and 30 Hz), 8.0 (1H, s), 8.24 (1H, s);

m/e: 284 (M+H+), 283, 255, 237, 216, 202 (100%), 192, 91, 83, 77, 70, 55.

EXAMPLE 15

This Example illustrates the preparation of Compound No. 16 of Table I, which is the methyl ether of Compound No. 3 of Table I.

To suspension of oil free sodium hydride (1 equivalent) in dry dimethylformamide (5ml per mmol) was added a solution of Compound No. 3 of Table I (1 equivalent; 1 g; 4 mmol) in dry dimethylformamide (2.5 ml per mmol) with stirring. Once the effervescence had subsided, methyl iodide (1 equivalent); 0.568 g, 4 mmol) was added and the mixture was heated at 80° C. for 4 hours. On cooling, the reaction mixture was poured into water and extracted with ether (2×100 ml). The combined organic layers were washed with water and saturated brine, dried over magnesium sulphate and the solvent removed. Flash chromatography (silica gel, petrol/ether elution) gave the product as a yellow oil (0.6 g, 57.5%).

Analysis: Found: C, 68.3; H, 9.7; N, 15.5. C$_{15}$H$_{25}$N$_3$O requires C, 68.4; H, 9.5; N, 16.0%);

IR: 3100, 2960, 1500, 1390, 1360, 1270, 1200, 1130, 1010, 950, 740 cm$^{-1}$;

NMR 990 MHz, CDCl$_3$) 0.98 (3H, t, J=7 Hz), 0.99 (9H, s), 1.5 (2H, dt, J=7 and 7Hz), 2.12 (2H, m), 2.56 (2H, m), 3.34 (3H, s), 4.52 (2H, dd, J=14.4 and 27Hz), 7.92 (1H, s), 8.22 (1H, s);

m/e: 264 (M+H+), 263, 206, 181 (100%).

EXAMPLE 16

The ethyl ether of Compound No. 3, Compound No. 17 of Table I, was prepared using the general method of Example 15. The product was a yellow oil (0.46g, 41.5%).

Analysis: (Found: C, 68.5; H, 9.8; N, 15.0. $C_{16}H_{27}N_3O$ requires C, 69.3; H, 9.8; N, 15.2%);

IR: 2980, 1400, 1370, 1325, 1200, 1140, 1020, 960, 800, 730 cm$^{-1}$;

NMR (90 MHz, CDCl$_3$): 0.98 (3H, t, J=7Hz), 0.99 (9H, s), 1.16 (3H, t, J=7Hz), 1.52 (2H, dt, J=7 and 7 Hz), 2.12 (2H, m), 2.58 (2H, m), 3.58 (2H, m), 4.52 (2H, dd, J=14 and 27 Hz), 7.94 (1H, s), 8.26 (1H, s);

m/e (CI): 278 (M+H$^+$), 220, 195.

EXAMPLE 17

The methyl ether of Compound No. 4; Compound No. 19 of Table I, was prepared using the general method of Example in which Compound No. 4 (1.05 g, 4mmol) and methyl iodide (0.568 g 4 mmol) were reacted at 80° C. for 4 hours and at room temperature for 16 hours. The product was a yellow oil (0.22 g, 20.05%).

Analysis: Found: C, 69.0; H, 10.4; N, 14.7. $C_{16}H_{27}N_3O$ requires C, 69.3; H, 9.8; N, 15.2%);

IR: 2960, 1500, 1460, 1370, 1275, 1200, 1140, 1090, 1020, 960, 760 cm$^{-1}$;

NMR (90 MHz, CDCl$_3$): 1.0 (9H, s), 1.1 (6H, d, J=7Hz), 1.81 (1H, m), 2.08 (2H, m), 2.62 (2H, m), 3.40 (3H, s), 4.55 (2H, dd, J=13.5 and 25 Hz), 7.96 (1H, s), 8.28 (1H, s);

m/e: 278 (M+H$^+$), 277, 220, 195 (100%), 182.

EXAMPLE 18

By the general method of Example 15, Compound No. 4 of Table I (2.0 g, 8 mmol) and allyl bromide (0.97 g, 8 mmol) were reacted at 80° C. for 4 hours and at room temperature for hours, to give Compound No. 20 of Table I as a yellow oil (0.44 g, 18.3%).

Analysis: Found: C, 69.0; H, 9.5; N, 13.4.

$C_{18}H_{29}N_3O$ requires C, 71.3; H, 9.6; N, 13.9%);

IR: 2960, 1640, 1400, 1370, 1270, 1210, 1140, 940, 860, 775 cm$^{-1}$;

NMR (90 MHz, CDCl$_3$): 0.96 (6H, d, J=7 Hz), 0.97 (9H, s), 1.61–1.9 (1H, m), 1.98–2.16 (2H, m), 2.56–2.7 (2H, m), 4.02–4.2 (2H, m), 4.56 (2H, dd, J=13.5 and 27 Hz), 5.04–5.26 (2H, m), 5.31–5.41 (1H, m), 7.92 (1H, s), 8.23 (1H, s);

m/e (CI): 303 (M$^+$), 246, 221.

EXAMPLE 19

Using the general method of Example 15, Compound No. 4 (2.0 g, 8mmol) and propargyl bromide (0.95 g, 8 mmol) were reacted at 80° C. for 16 hours to give Compound No. 21 of Table I as a yellow oil (0.38 g, 15.9%).

Analysis: Found: C, 71.2; H, 9.0; N, 13.6. $C_{18}H_{27}N3O$ requires C, 71.8; H, 9.0; N, 14.0%);

IR: 3300, 2960, 2220, 1370, 1275, 1210, 1140, 1080, 955, 770, 670 cm$^{-1}$;

NMR (90 MHz, CDCl$_3$): 1.0 (6H, d, J=7 Hz), 1.01 (9H, s), 1.6–1.98 (1H, m), 2.0–2.2 (2H, m), 2.42 (1H, t, J=1.8 Hz), 4.34 (2H, d, J=1.8 Hz), 4.57 (2H, dd, J=14.4 and 26 Hz,), 7.95 (1H, s), 8.39 (1H, s);

m/e: 302 (M+H$^+$), 244, 219, 206.

EXAMPLE 20

Using the general method of Example 15, Compound No 4 (2.0 g, 8 mmol) and benzyl chloride (1.01 g, 8 mmol) were reacted at 80° C. for 16 hours to give Compound No. 22 as a yellow oil (0.7 g, 24.8%).

Analysis, Found: C, 74.5; H, 9.1; N, 11.9. $C_{22}H_{31}N_3O$ requires C, 74.8; H, 8.8; N, 11.9%);

IR: 2960, 1730, 1500, 1450, 1360, 1270, 1200, 1130, 1080, 950, 730, 695, 6.75 cm$^{-1}$;

NMR (90 MHz, CDCl$_3$): 0.96 (6H, d, J=7 Hz), 1.01 (9H, s), 1.6–1.98 (1H, m), 2.0–2.2 (2H, m), 2.68–2.78 (2H, m), 4.62 (2H, dd, J=14.4 and 1.6 Hz), 4.63 (2H, dd, J=10.8 and 18.9 Hz), 7.32 (5H, s), 7.92 (1H, s), 8.16 (1H, s);

m/e: (CI): 353 (M$^+$), 310, 296, 271, 258.

EXAMPLE 21

To a solution of Compound No. 4 of Table I (2.0 g, 8 mmol) in dry tetrahydrofuran (40 ml) at −78° C. was added n-butyl lithium (3 ml of 2.6M, 8 mmol). After stirring for 30 minutes the resulting solution was treated with benzoyl chloride (1.12 g, 8 mmol) and then refluxed for 1 hour. On cooling, the reaction mixture was poured onto ice and extracted with ether (2×100 ml). The combined organic extracts were washed with water and saturated brine then dried over magnesium sulphate before removing the solvent. Flash chromatography (silica gel, petrol/ether elution) of the resulting residue gave Compound No. 28 of Table I as a yellow oil (0.64 g, 22.95%).

Analysis: Found: C, 71.7; H, 7.8; N, 10.7. $C_{22}H_{29}N_3O$ requires C, 71.9; H, 7.9; N, 11.4%);

IR: 2960, 1720, 1600, 1500, 1450, 1400, 1370, 1270, 1170, 1140, 1110, 950, 710, 670 cm$^{-1}$;

NMR (90 MHz, CDCl$_3$): 0.86 (6H, d, J=6.3 Hz), 1.16 (9H, s), 1.56 (1H, m), 1.88 (2H, m), 3.04 (2H, t, J=1.8 Hz), 5.01 (2H, dd, J=14.4 and 22.5 Hz), 7.48 (3H, m), 7.86 (1H, s), 8.00 (2H, m), 8.18 (1H, s);

m/e: 367 (M$^+$), 325, 245, 203, 105, 77.

EXAMPLE 22

This Example illustrates the preparation of 2,2-dimethyl-3-hydroxy-3-(5-chloro-pent-2yne-1yl)-4-(1,2,4-triazol-1-yl)-butane (Compound No. 23 in Table I).

Stage 1

Preparation of 1-(1-butyldimethylsiloxy)-but-3-yne.

To a stirred solution of t-butyl-dimethylsilyl chloride (10.9 g, 72 mmol) and imidazole (4.5 g, 66 mmol) in dimethyl formamide (25 ml) was added a solution of but-3-yn 1-ol (4.6 g, 66 mmol) in dichloromethane (25 ml). The mixture was stirred at 40° C. for 7½ hours, then cooled to room temperature and partitioned between diethyl ether and water. The aqueous portion was extracted with diethyl ether, then the combined ethereal extracts were washed with water and brine, dried over anhydrous magnesium sulphate and concentrated in vacuo to give a yellow oil (12 g). The product was used with no further purification.

Stage 2

Preparation of the 1-butyldimethylsiloxy derivative of the title compound.

To a solution of 1-(t-butyldimethylsilyloxy)-but-3-yne (4.6 g, 25 mmol) in dry tetrahydrofuran (35 ml), at room temperature under nitrogen, was added ethyl magnesium bromide (8.5 ml of a 3.0 molar solution in diethyl ether). After an initial exothermic reaction the reaction mixture was heated under reflux for 15 minutes, then cooled to room temperature. A solution of the product of Stage 1 of Example 1 (3.0 g, 17 mmol) in tetrahydrofuran (25 ml) was added and the mixture heated under reflux for 2 hours. The reaction mixture was partitioned between ethyl acetate and 20% ammonium chloride solution. The aqueous portion was further extracted with ethyl acetate, then the combined organic extracts were washed with water and brine, dried over anhydrous magnesium sulphate and concentrated in vacuo to give a dark yellow oil (7.5 g). Column chromatography of the crude product on silica gel eluting with diethyl ether (10–50%) in petrol gave the 1-butyldimethylsiloxy derivative as an orange oil (3.8 g).

Stage 3

Preparation of 2,2-dimethyl-3-hydroxy-3-(5-hydroxy-pent-2-yne-lyl)-4-(1,2,4-triazol-1-yl)-butane.

To a solution of the product of Stage 2 (2.9 g, 8 mmol) in dry tetrahydrofuran (5 ml), at room temperature under nitrogen, was added a spatula full of 4 A molecular sieves. After 5 minutes tetra-n-butylammoniumfluoride (8.7 ml of a 1.0 molar solution in tetrahydrofuran) was added and the reaction mixture was stirred at room temperature for 4 hours. The reaction mixture was diluted with ethyl acetate, and water (2 ml) was added. The mixture was filtered through 'Hyflo', dried over magnesium sulphate and evaporated to dryness. Column chromatography of the crude product on silica gel eluting with ethyl acetate (20–100%) in petrol gave the hydroxy derivative as a yellow gum (1.5 g).

Stage 4

To a stirred solution of the product of Stage 3 (1.14 g, 4.5 mmol) and triethylamine (1.1 ml, 8 mmol) in dichloromethane (15 ml), at room temperature, was added dropwise a solution of methanesulphonyl chloride (0.45 ml, 5.4mmol) in dichloromethane (5 ml). The reaction mixture was stirred at room temperature for 2½ hours, then diluted with dichloromethane (5 ml). The react stirred at room temperature for 2½ hours, then diluted with dichloromethane and washed with 1M citric acid solution, water, saturated sodium bicarbonate solution and brine, dried over anhydrous magnesium sulphate and concentrated in vacuo to give the methanesulphonate derivative , as a yellow gum (1.4 g). The product was unstable, and was used immediately in the next step, without purification.

Stage 5

A mixture of the product of Stage 4 (1 g, 3 mmol) and lithium chloride (0.4 g, 9.5 mmol) in dimethylsulphoxide (10 ml) was stirred and heated at 60° C for 3 hours. The reaction mixture was partitioned between ethyl acetate and water. The organic layer was washed with water and brine, dried over magnesium sulphate and concentrated in vacuo. Column chromatography of the crude product on silica gel eluting with ethyl acetate (20–70%) in petrol gave the title compound, as a pale yellow gum (0.67 g).

NMR (CDCl$_3$, 270 MHz): 1.08 (9H, s), 2.12 (1H, m), 2.54 (3H, m), 3.54 (2H, t), 3.63 (1H, s), 4.30 (1H, d), 4.60 (1H, d), 7.94 (1H, s), 8.26 (1H, s).

m/e: 270 (MH+), 234, 220, 212, 187, 168, 150, 83, 70, 57, 43.

IR (film): 3150–3700, 3120 cm$^{-1}$.

Analysis( C$_{13}$H$_{20}$N$_3$O, Cl, Requires: (C, 57.88; H, 7.47; N, 15.58% Found: C, 57.49; H, 7.60; N, 15.30%.

EXAMPLE 23

Compound No. 25 of Table I was prepared using the general method of Example 22. The product was a 1:1 mixture of diastereoisomers, characterised as follows:

NMR (CDCl$_3$, 270 MHz): 0.84 (3H, t), 1.12 (9H, s), 1.50 (2H, m) 1.85 (2H, m), 2.04 (1H, m), 2.64 (1H, d), 3.92 and 3.95 (1H, 2s—isomers), 4.3 (1H, d), 4.5 (1H, m), 4.64 (1H, m), 7.98 (1H, s), 8.3 (1H, s).

IR (film): 3150–3600, 3120, 2220 cm$^{-1}$.

m/e: No M+, 262, 240, 228, 168, 150, 109, 83, 70, 57.

EXAMPLE 24

Compound No. 26 of Table I was prepared using the general method of Example 22. The product was a 1:1 mixture of diastereoisomers, characterised as follows:

NMR (CDCl$_3$, 270 MHz): 1.0 (3H, t), 1.1 (9H, s), 1.8 (2H, m), 2.1 (1H, m), 2.55 (3H, m), 3.68 and 3.71 (1H, 25—for isomers , 3.9 (1H, m), 4.3 (1H, d), 4.64 (1H, d), 7.95 (1H, s), 8.3 (1H, s).

IR (film): 3150–3650, 3120 cm$^{-1}$.

m/e: No M+, 262, 240, 168, 150, 83, 70, 57.

The manner in which the compounds of the present invention may be formulated into compositions suitable for application is shown generally in the following indicative illustrations numbered as Examples 10 to 19.

EXAMPLE 25

An emulsifiable concentrate is made up by mixing the following ingredients, and stirring the mixture until all the constituents were dissolved.
Compound of Table I: 10%
Calcium dodecylbenzenesulphate: 5%
"SYNPERONIC" NP13: 5%
"Aromasol" H: 80%

EXAMPLE 26

A composition in the form of grains readily dispersible in a liquid, e.g. water, is prepared by grinding together the first three ingredients in the presence of added water and then mixing in the sodium acetate. The resultant mixture is dried and passed through a British Standard mesh sieve, size 44–100, to obtain the desired size of grains.
Compound of Table I: 50%
"Dispersol" T: 25%
"SYNPERONIC" NP5: 1.5%
Sodium acetate: 23.5%

EXAMPLE 27

The following ingredients are ground together to produce a powder formulation readily dispersible in liquids.
Compound of Table I: 45%
"Dispersol" T: 5% "SYNPERONIC" NX: 0.5%
"Cellofas" B600: 2%
China clay GTY powder: 47.5%

EXAMPLE 28

The active ingredient is dissolved in acetone and the resultant liquid is sprayed on to the granules of attapulgite clay. The solvent is then allowed to evaporate to produce a granular composition.
Compound of Table I: 5% Attapulgite granules: 95%

EXAMPLE 29

A composition suitable for use as a seed dressing is prepared by mixing the three ingredients.
Compound of Table I: 50%
Mineral oil: 2%
China clay: 48%

EXAMPLE 30

A dusting powder is prepared by mixing the active ingredient with talc.
Compound of Table I: 5%
Talc: 95%

EXAMPLE 31

A flowable formulation is prepared by bead-milling the constituents set out below and then forming an aqueous suspension of the ground mixture with water.
Compound of Table I: 40%
"Dispersol" T: 4%
"SYNPERONIC" NP5: 1%
Water: 55%

EXAMPLE 32

A dispersible powder formulation is made by mixing together the ingredients set out below and then grinding the mixture until all were thoroughly mixed.
Compound of Table I: 25%
"Aerosol" TO/B: 2%
"Dispersol" A.C.: 5%
China clay: 28%
Silica: 40%

EXAMPLE 33

This Example illustrates the preparation of a dispersible powder formulation. The ingredients are mixed and the mixture then ground in a comminution mill.
Compound of Table I: 25%
"PERMINAL" BX: 1%
"Dispersol" T: 5%
Polyvinylpyrrolidone: 10%
Silica: 25%
China clay: 34%

EXAMPLE 34

The ingredients set out below are formulated into dispersible powder by mixing then grinding the ingredients.
Compound of Table I: 25% "Aerosol" TO/B: 2% "Dispersol" A: 5%
China clay: 68%

In Examples 25 to 34 the proportions of the ingredients given are by weight.

There now follows an explanation of the compositions or substances re-resented by the various Trade Marks and Trade Names mentioned above. "SYNPERONIC" NP13: a condensate of nonyl phenol (1 mole) with ethylene oxide (13 moles).
"AROMASOL" H: a solvent mixture of alkylbenzenes.
"DISPERSOL" T AND AC: a mixture of sodium sulphate and a condensate of formaldehyde with sodium naphthalene sulphonate.
"SYNPERONIC" NP5: a condensate of nonyl phenol (1 mole) with naphthalene oxide (5.5 moles).
CELLOFAS B600: a sodium carboxymethyl cellulose thickener.

EXAMPLE 35

Whole Plant Screen

Compound numbers indicated in Table V were tested on a whole plant screen. The compounds were testd for plant growth regulator activity against five species (Table IV) for various growth effects relevant to plant growth regulation.

Methodology

The plant species used in this screen are presented in Table II with the leaf stage at which they were sprayed. Each chemical was applied at 4000 ppm (4 kg/ha in a 1000 L/ha field volume) using a tracksprayer and a SS8004E (Teejet) nozzle.

After spray the plants were grown in a glasshouse with 25° C. day/22° C. night temperatures. The exception to this were the temperature cereals, wheat and barley which are grown in 13°–16° C. day/11°–13° C. night temperatures. Supplementary lighting was supplied when necessary to provide an average photoperiod of 16 hours (14 hours minimum).

After 2–6 weeks in the glasshouse, depending on species and time of year, the plants were visually assessed for morphological characteristics. Formulation blanks were used as controls to assess the plants against. The results are presented in Table V.

TABLE IV

| | | Plant Material used for Whole Plant Screen | | | |
|---|---|---|---|---|---|
| Species | Code | Variety | Growth Stage at Treatment | No. Plants per 3" Pot | Compost Type |
| Barley | BR | Atem | 1–1.5 leaves | 4 | JIP* |
| Wheat | WW | Timmo | 1–1.5 leaves | 4 | JIP |
| Maize | MZ | Earliking | 2¼–2½ leaves | 1 | PEAT |
| Apple | AP | Red Delicious | 4–5 leaves | 1 | JIP |
| Rice | RC | Ishikari | 2–2½ leaves | 4 | JIP |

JIP* = John Innes Potting Compost

TABLE V

| SPECIES | COMPOUND NO. | R | G | A | T | I |
|---|---|---|---|---|---|---|
| BR | 1 | 2 | 1 | | 1 | 3 |
| | 2 | 1 | | | | 1 |
| | 3 | 3 | 1 | | 2 | 3 |
| | 4 | 3 | 1 | | 2 | 3 |
| | 5 | 3 | 1 | | 2 | 3 |
| | 6 | 2 | 1 | | 1 | 3 |
| | 7 | 2 | | | | 3 |
| | 8 | | | | | 1 |
| | 9 | 1 | | | 1 | 2 |
| | 10 | 2 | 2 | | | 3 |
| | 11 | 2 | | | | 3 |
| | 12 | 2 | 1 | | 3 | 3 |
| | 18 | 2 | 1 | | | 2 |
| | 23 | 3 | 2 | | | 3 |
| | 24 | 3 | 2 | | 2 | 3 |
| WW | 1 | 2 | 1 | | | 3 |
| | 2 | 2 | 1 | | 1 | 3 |
| | 3 | 2 | 2 | | | 3 |
| | 4 | 2 | 2 | | | 3 |
| | 5 | 2 | 2 | | | 3 |
| | 6 | 2 | 1 | | | 3 |
| | 7 | 1 | | | | 3 |
| | 8 | 2 | | | 2 | 2 |
| | 9 | 2 | | | 2 | 2 |
| | 10 | 3 | | | | 3 |
| | 11 | 3 | 2 | | 1 | 3 |
| WW | 12 | 3 | 2 | | 2 | 3 |
| | 18 | 2 | 1 | | 1 | 3 |
| | 23 | 2 | 2 | | 2 | 3 |
| | 24 | 2 | 2 | | 3 | 3 |
| RC | 1 | 2 | 2 | | 1 | 3 |
| | 2 | 1 | | | | 1 |
| | 3 | 2 | 2 | | 1 | 3 |
| | 4 | 2 | 2 | | 2 | 3 |
| | 5 | 2 | 2 | | 1 | 3 |
| | 6 | 2 | 2 | | 3 | 3 |
| | 7 | 2 | 1 | | 3 | 2 |
| | 8 | 1 | | | 0 | 3 |
| | 9 | 2 | 1 | | 0 | 3 |
| | 10 | 3 | 2 | | 3 | 3 |
| | 11 | 2 | | | 0 | 2 |

TABLE V-continued

| SPECIES | COMPOUND NO. | R | G | A | T | I |
|---|---|---|---|---|---|---|
| | 12 | 3 | | | 2 | 3 |
| | 18 | 2 | 1 | | 0 | 3 |
| | 23 | 2 | 1 | | 2 | 3 |
| | 24 | 3 | 1 | | | 3 |
| MZ | 1 | 2 | 1 | | | 2 |
| | 2 | | | | | |
| | 3 | | | | | |
| | 4 | 2 | 2 | | | 3 |
| | 5 | 1 | 1 | | 1 | 1 |
| | 6 | 2 | 1 | 1 | | 1 |
| MZ | 7 | | | | | 1 |
| | 8 | | | — | — | |
| | 9 | | | — | — | |
| | 10 | 2 | | 1 | — | 2 |
| | 11 | | | — | — | |
| | 12 | | | | — | — |
| | 18 | 2 | | | | 2 |
| | 23 | 1 | | | | |
| | 24 | | | | | |
| AP | 1 | 3 | 1 | | | 3 |
| | 2 | | | | | |
| | 3 | 1 | | | | 1 |
| | 4 | 2 | 1 | 3 | 1 | 2 |
| | 5 | 2 | | | | 3 |
| | 6 | 3 | | | | 3 |
| | 7 | | | | | |
| | 8 | | | | | |
| | 9 | 2 | | | | 1 |
| | 10 | 2 | 1 | | | 2 |
| | 11 | 2 | | | | 2 |
| | 12 | 2 | | | | 2 |
| | 18 | | 1 | | | |
| | 23 | 1 | 1 | | | 1 |
| | 24 | | 1 | | | |

Key:
R = Retardation
G = Greening effect
A = Apical damage
T = Tillering or side shooting
I = Interligular or internodal length reduction
All effects are scored visually on 1-3 basis where
1 = 10-30%
2 = 31-60%
3 = 61-100%
Blank means less than 10% effect.

EXAMPLE 26

Intermediate Retardant Test

Methodology

Three species are involved in this test RICE, SPRING-BARLEY and APPLES. The variety and growth stages at spray are outlined in Table VI. Compounds were applied at 1000 ppm and 4000 ppm respectively (1 kg and 4 kg ha$^{-1}$ at a field volume of 1000 ha$^{-1}$) or at 500 ppm and 2000 ppm respectively as an overall spray. This gives a foliar and root component in the test, i.e. this test will detect the activity of both root and foliar acting compounds. The rice was grown in 4" 'paddy' pots, i.e. the roots and bottom of the stems are immersed in water under conditions corresponding to those in paddy fields. Spring barley and apples were grown in 4" pots. The plants were assessed for height to top-most ligule at approximately 28 days after treatment for spring barley and rice and for height to apex between 14 and 28 days after treatment for apples, (depending on time of year and growth stage). The results are presented in Table VII to IX. In each case the result for the 1000 ppm and 4000 ppm test for each compound is compared to the height of the formulation blank in that test, presented as a percentage reduction in height compared to the formulation blank.

TABLE VI

Plant Material for Intermediate Retardant Test

| Species | Variety | Growth Stage at Treatment | No. Plants per 4" Pot | Compost Type |
|---|---|---|---|---|
| Spring Barely | Atem | 3 leaves | 4 | JIP 1 |
| Rice | Ishikari | 3-4 leaves | 2 | SM2:JIP 1 |
| Apples | Red Delicious | 5-10 cm high | 1 | SM2:JIP 1 |

JIP 1 = John Innes Potting Compost
SM2 = a mixture of loam and grit

TABLE VIII

Percentage Reduction in Height of Spring Barley. (Compared to formulation blank).

| | RATE | | | |
|---|---|---|---|---|
| COMPOUND NO. | 500 ppm | 1000 ppm | 2000 ppm | 4000 ppm |
| 1 | — | 56 | — | 83 |
| 2 | — | 23 | — | 43 |
| 3 | — | 59 | — | 85 |
| 4 | — | 55 | — | 86 |
| 5 | — | 61 | — | 83 |
| 6 | — | 61 | — | 75 |
| 7 | — | 17 | — | 38 |
| 8 | — | 0 | — | 27 |
| 9 | — | 1 | — | 43 |
| 10 | — | 26 | — | 58 |
| 11 | — | 15 | — | — |
| 12 | 10 | — | 51 | — |
| 23 | 12 | — | 45 | — |
| 24 | 16 | — | 54 | — |

TABLE VII

Percentage Reduction in Height of Rice. (Compared to formulation blank).

| | RATE | | | |
|---|---|---|---|---|
| COMPOUND NO. | 500 ppm | 1000 ppm | 2000 ppm | 4000 ppm |
| 1 | — | 58 | — | 70 |
| 2 | — | 34 | — | 51 |
| 3 | — | 39 | — | 67 |
| 4 | — | 62 | — | 76 |
| 5 | — | 35 | — | 59 |
| 6 | — | 51 | — | 67 |
| 7 | — | 36 | — | 61 |
| 8 | — | 8 | — | 38 |
| 9 | — | 43 | — | 51 |
| 10 | — | 42 | — | 64 |
| 11 | — | 17 | — | — |
| 12 | 33 | — | 55 | — |
| 18 | 20 | — | 44 | — |
| 23 | 26 | — | 41 | — |
| 24 | 42 | — | 53 | — |

TABLE IX

Percentage Reduction in Height of Apples. (Compared to formulation blank).

| | RATE | | | |
|---|---|---|---|---|
| COMPOUND NO. | 500 ppm | 1000 ppm | 2000 ppm | 4000 ppm |
| 1 | — | 13 | — | 45 |
| 2 | — | 3 | — | 14 |
| 3 | — | 8 | — | 38 |
| 4 | — | 3 | — | 22 |
| 5 | — | 8 | — | 32 |
| 6 | — | 50 | — | 54 |
| 7 | — | 24 | — | 38 |

TABLE IX-continued

Percentage Reduction in Height of Apples.
(Compared to formulation blank).

| COMPOUND NO. | RATE | | | |
|---|---|---|---|---|
| | 500 ppm | 1000 ppm | 2000 ppm | 4000 ppm |
| 8 | — | 2 | — | 13 |
| 9 | — | 7 | — | 37 |
| 10 | — | 25 | — | 64 |
| 11 | — | 16 | — | — |
| 12 | 0 | — | 19 | — |
| 18 | 0 | — | 14 | — |

EXAMPLE 37

In this Example, Compound Nos. 3, 4 and 6 of the present invention were compared with Compound No. 4 of EP 0097425 which is stated to be an especially preferred compound. The compounds were tested in side by side comparison using the method of Example 36 with application rates of 500 ppm and 2000 ppm respectively for rice and spring barley. For apples, an application rate 2000 ppm was used, but was applied as a foliar only spray and a root drench respectively. The results are presented in Tables X to XIII and clearly demonstrate the surprising superiority of the compounds of the present invention.

TABLE X

Percentage Reduction in Height of Spring Barley.
(Compared to formulation blank).

| COMPOUND NO. | RATE | |
|---|---|---|
| | 500 ppm | 2000 ppm |
| 3 | 23 | 63 |
| 4 | 32 | 65 |
| 6 | 28 | 59 |
| No. 4 of EP 0097425 | 10 | 13 |

TABLE XI

Percentage Reduction in Height of Rice.
(Compared to formulation blank).

| COMPOUND NO. | RATE | |
|---|---|---|
| | 500 ppm | 2000 ppm |
| 3 | 33 | 54 |
| 4 | 45 | 52 |
| 6 | 36 | 58 |
| No. 4 of EP 0097425 | 15 | 22 |

TABLE XIII

Percentage Reduction in Height of Apples.
(Compared to formulation blank).

| COMPOUND NO. | RATE | |
|---|---|---|
| | 500 ppm | 2000 ppm |
| 3 | 6 | 58 |
| 4 | 5 | 25 |
| 6 | 0.4 | 63 |
| No. 4 of EP 0097425 | 9 | 6 |

I claim:

1. A triazole having the formula (I):

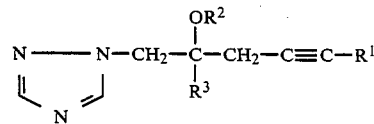

and stereoisomers thereof, wherein $R^1$ is a branched or straight chain alkyl group containing from 3 to 5 carbon atoms or a haloalkyl group containing from 2 to 4 carbon atoms or a group $-(CH_2)n-R^4$ where n is from 0 to 2 and $R^4$ is cyclopropyl, cyclobutyl, cyclopentyl or cyclohexyl; $R^2$ is hydrogen, an alkyl group containing from 1 to 4 carbon atoms, an alkenyl group containing from 2 to 4 carbon atoms, an alkynyl group containing from 2 to 4 carbon atoms, an alkynyl group containing from 2 to 4 carbon atoms or a benzyl group; and $R^3$ is a tertiary butyl group optionally substituted by one or more halogen atoms; and acid addition salts, acetate and benzoate esters and metal complexes of the compounds of formula (I) wherein $R^2$ is hydrogen.

2. A triazole derivative according to claim 1 wherein $R^1$ is a branched or straight chain alkyl group containing from 3 to 4 carbon atoms.

3. A triazole derivative according to claim 1 wherein $R^1$ is the group $-(CH_2)_n-R^4$ and n is 0 or 1.

4. A triazole derivative according to any of the preceding claims wherein $R^2$ is hydrogen or methyl.

5. A triazole derivatives according to claim 1 wherein $R^3$ is a tertiary butyl group optionally substituted by a single fluorine, chlorine or bromine atom.

6. A plant growth regulating composition comprising an effective amount of a triazole derivative according to claim 1 and, an inert carrier or diluent.

7. A method of regulating plant growth which comprises applying to the plant, to the seed of a plant, or to the locus of the plant or seed an effective amount of a triazole derivative according to claim 1.

* * * * *